US007290451B2

United States Patent
Taniguchi et al.

(10) Patent No.: US 7,290,451 B2
(45) Date of Patent: Nov. 6, 2007

(54) STATUS DISCRIMINATING APPARATUS OF HUMAN, ANIMAL, MACHINE OR THE LIKE USING ULTRASONIC VIBRATION DETECTING SENSOR, AND STATUS DISCRIMINATING METHOD OF HUMAN, ANIMAL, MACHINE OR THE LIKE USING THE SAME

(75) Inventors: Kazuhiko Taniguchi, Souraku-gun (JP); Tomoyuki Sawayama, Kawanishi (JP)

(73) Assignee: Kinden Corporation, Osaka-shi (JP)

( * ) Notice: Subject to any disclaimer, the term of this patent is extended or adjusted under 35 U.S.C. 154(b) by 602 days.

(21) Appl. No.: 10/719,026

(22) Filed: Nov. 24, 2003

(65) Prior Publication Data

US 2004/0236218 A1 Nov. 25, 2004

(30) Foreign Application Priority Data

Jan. 17, 2003 (JP) .............................. 2003-009041

(51) Int. Cl.
*G01N 29/00* (2006.01)
*G01V 13/00* (2006.01)
(52) U.S. Cl. .......................................... 73/602; 73/599
(58) Field of Classification Search .......... 73/596–602, 73/627–630, 615, 290 V
See application file for complete search history.

(56) References Cited

U.S. PATENT DOCUMENTS

| 4,566,330 A | * | 1/1986 | Fujii et al. ..................... 73/599 |
| 4,575,799 A | * | 3/1986 | Miwa et al. ................. 600/442 |
| 5,456,255 A | * | 10/1995 | Abe et al. ..................... 600/443 |
| 5,515,339 A | * | 5/1996 | Noda ........................... 367/100 |
| 5,834,648 A | * | 11/1998 | Wang et al. ................... 73/606 |
| 6,295,873 B1 | * | 10/2001 | Condreva ....................... 73/597 |

(Continued)

FOREIGN PATENT DOCUMENTS

JP 58-071417 * 4/1983

(Continued)

OTHER PUBLICATIONS

Technos, Technos Japan Risyo Sensor. Bed Leaving Alarm, Jan. 2006.

(Continued)

*Primary Examiner*—Helen Kwok
(74) *Attorney, Agent, or Firm*—Griffin & Szipl, P.C.

(57) ABSTRACT

A human or other status discriminating apparatus includes an ultrasonic vibration detecting sensor comprising a container main body, a liquid packed tightly in the container main body, and an ultrasonic vibrator for transmitting ultrasonic waves into the liquid and receiving ultrasonic waves reflected from the liquid surface, to detect behavior of a subject, an ultrasonic transmission and reception control device including an ultrasonic transmitter/receiver, a signal converter, and a microcomputer, for issuing a transmission signal at specific time intervals to the ultrasonic detecting sensor, receiving a reception signal at specific time intervals from the ultrasonic detecting sensor, and calculating risk associated with the detection object from the change of maximum amplitude of the input reception signal, and a cable for coupling the ultrasonic detecting sensor and ultrasonic transmission and reception control device, and forming an input and output passage of transmission signal and reception signal.

7 Claims, 9 Drawing Sheets

U.S. PATENT DOCUMENTS

| | | | |
|---|---|---|---|
| 6,397,656 B1 * | 6/2002 | Yamaguchi et al. | 73/1.82 |
| 6,591,680 B2 * | 7/2003 | Batzinger et al. | 73/598 |
| 6,621,278 B2 * | 9/2003 | Ariav | 324/637 |
| 6,684,703 B2 * | 2/2004 | Chatellier et al. | 73/600 |

FOREIGN PATENT DOCUMENTS

| | | |
|---|---|---|
| JP | 2002-118842 A | 4/2002 |
| JP | 2003-315030 A | 11/2003 |
| JP | 2004-294190 * | 10/2004 |

OTHER PUBLICATIONS

L.A. Zadeh, Fuzzy Sets, Department of Electrical Engineering and Electronics Research Laboratory, University of California, Berkeley, California, pp. 29-44.

Takek, Bed Leaving Alarm.

Takayuki Ishikawa et al., A Study on Sleep Stage Estimation via Non-invasive Air Mattress Sensor, SICE Annual Conference in Fukui, Aug. 4-6, 2003, Fukui University, Japan, pp. 1414-1417.

* cited by examiner

[Fig. 1]
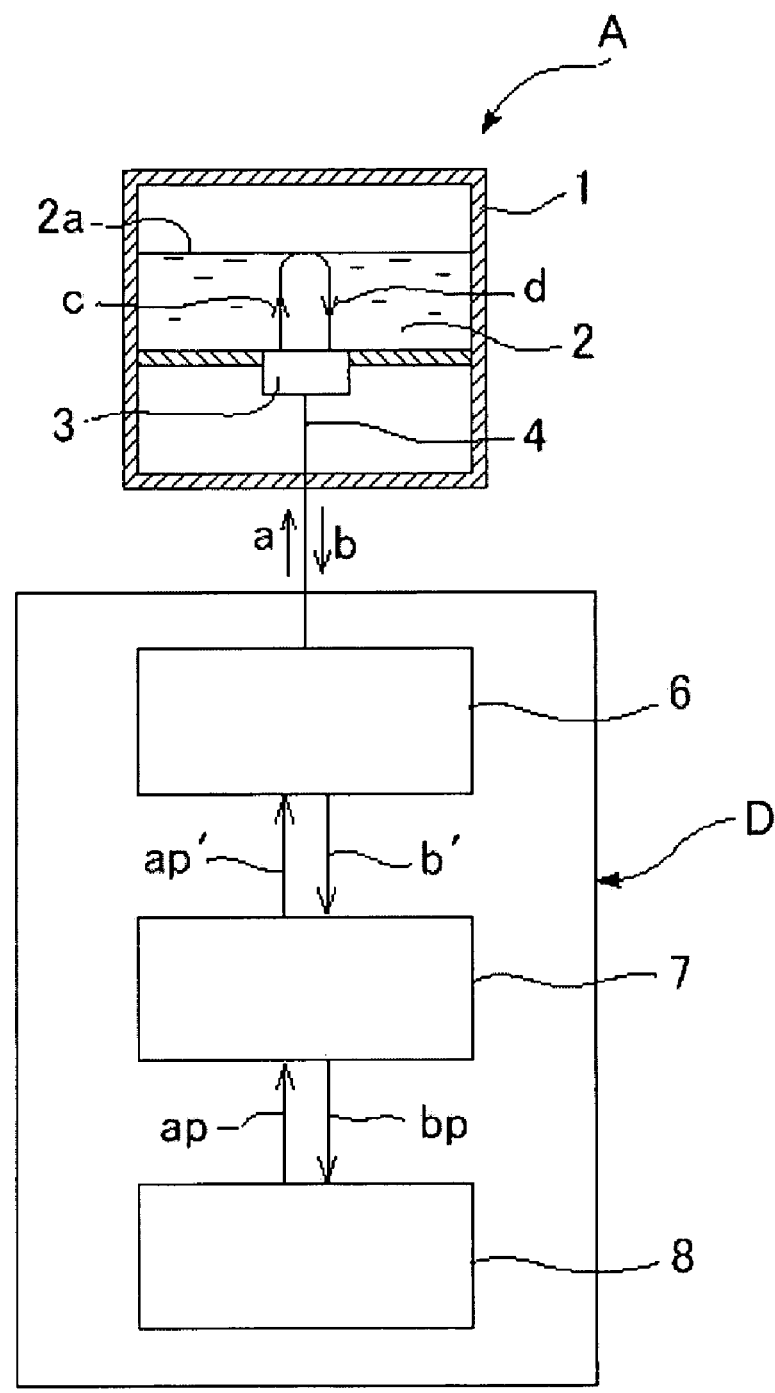

[Fig.2]
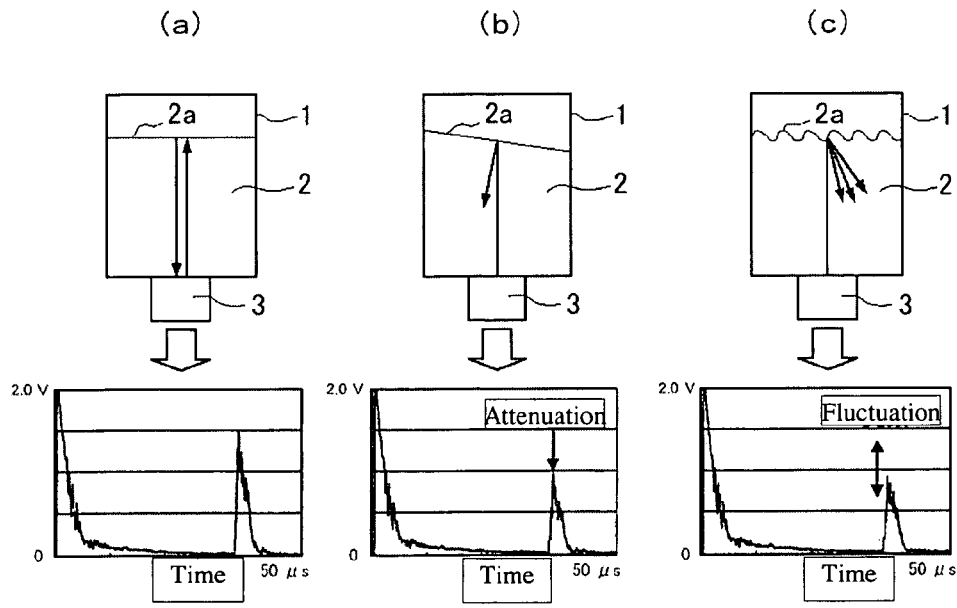
[Fig.3]
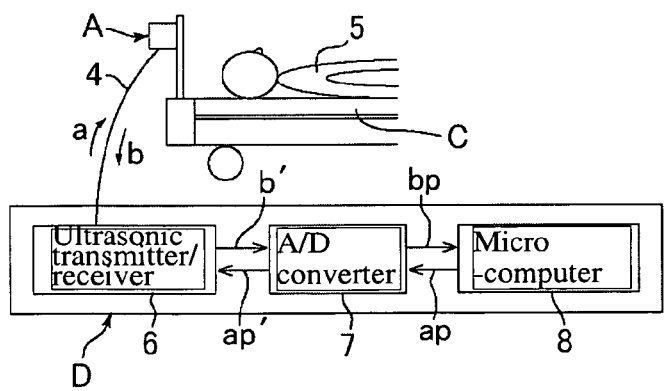
[Fig.4]
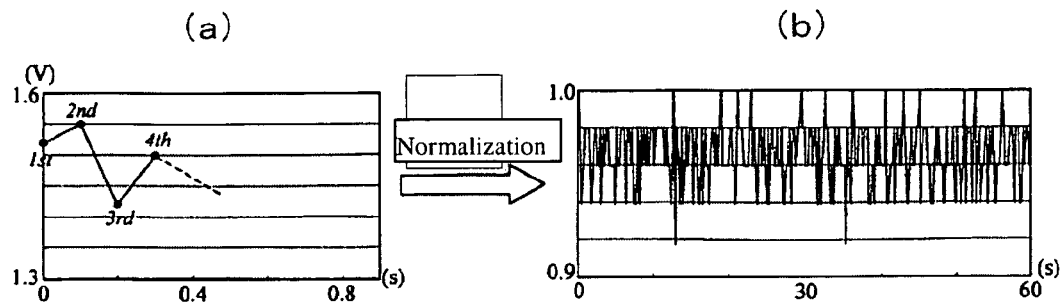

[Fig.5]
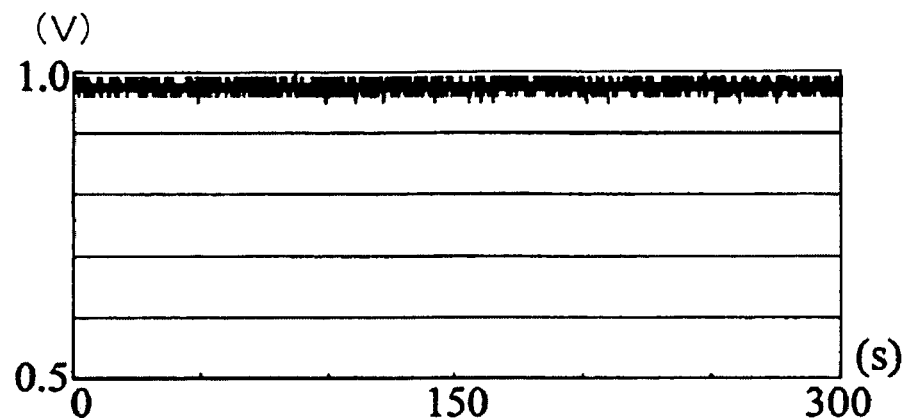
[Fig.6]
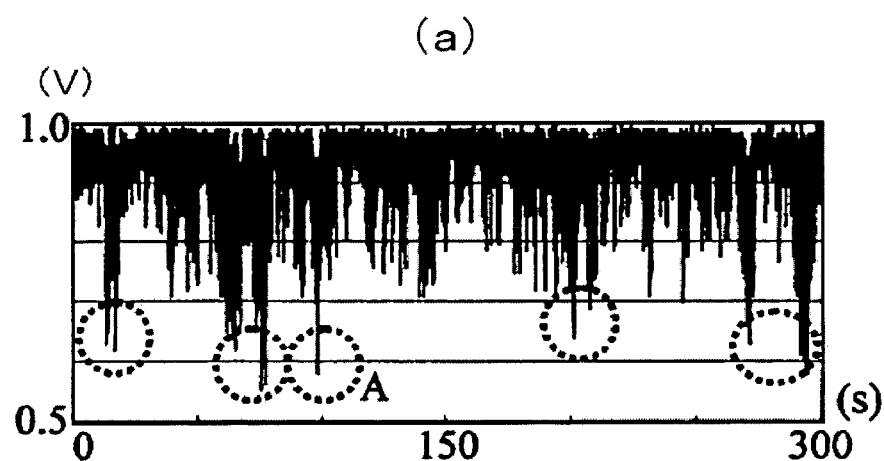
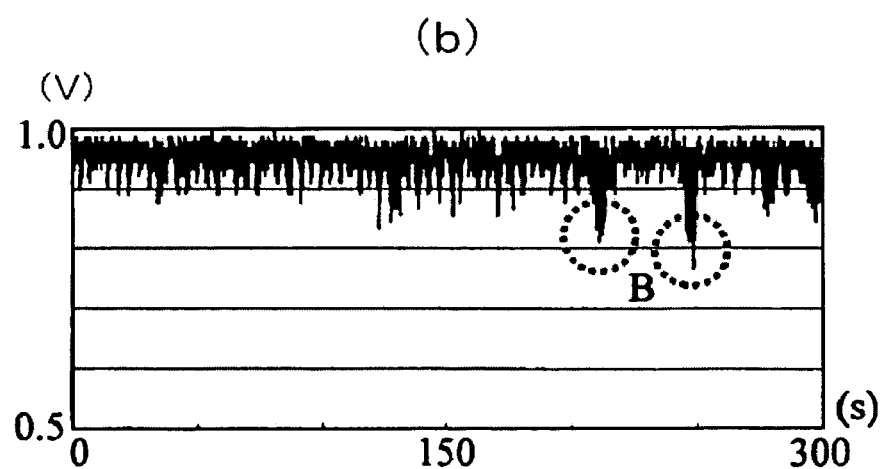

[Fig.7]
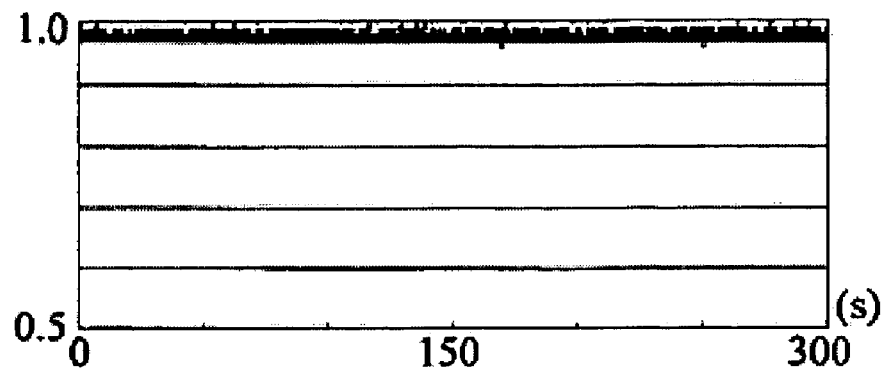
(a)
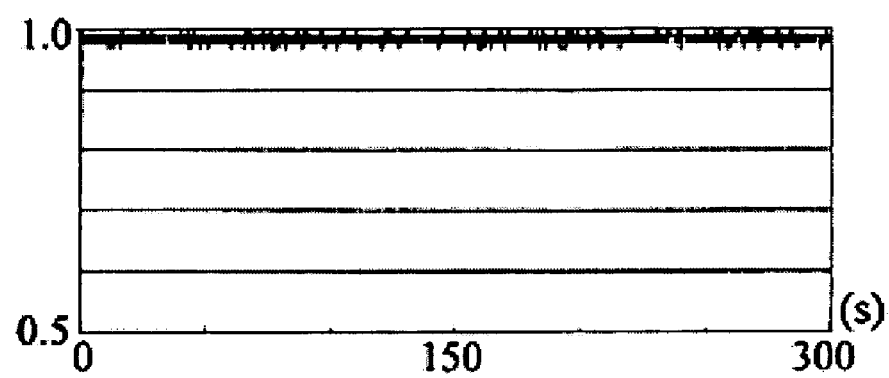
(b)
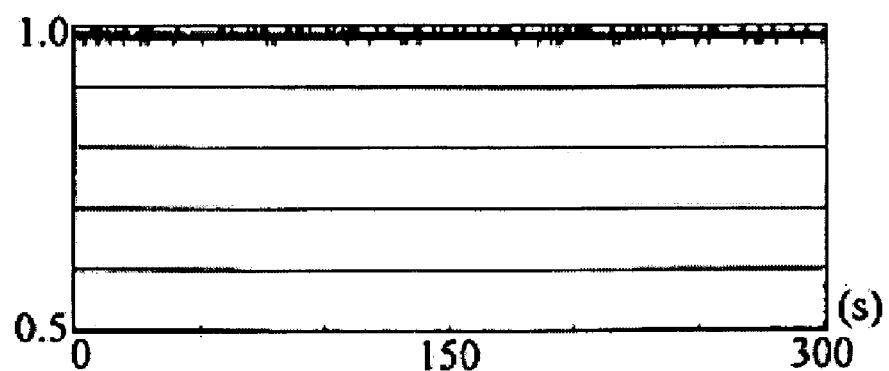
(c)

[Fig.8]
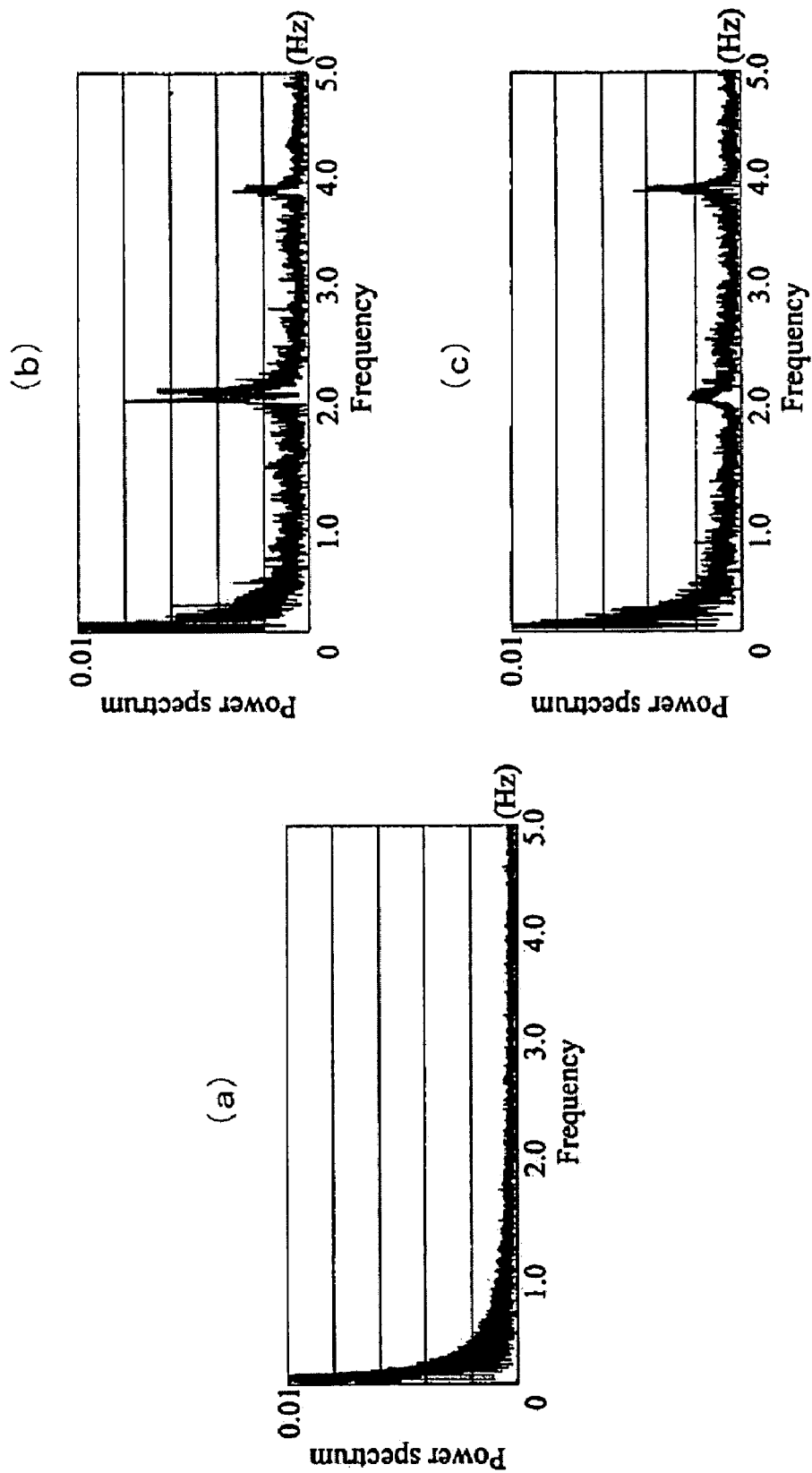

[Fig.9]
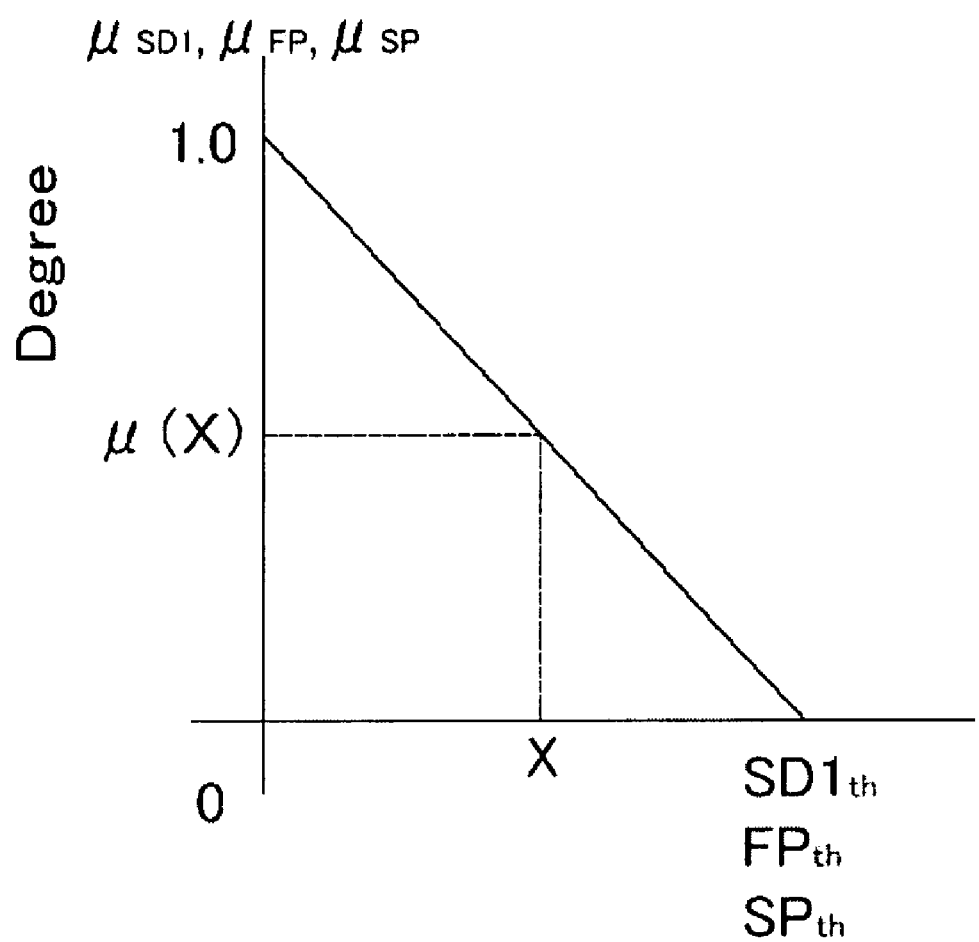

[Fig.10]
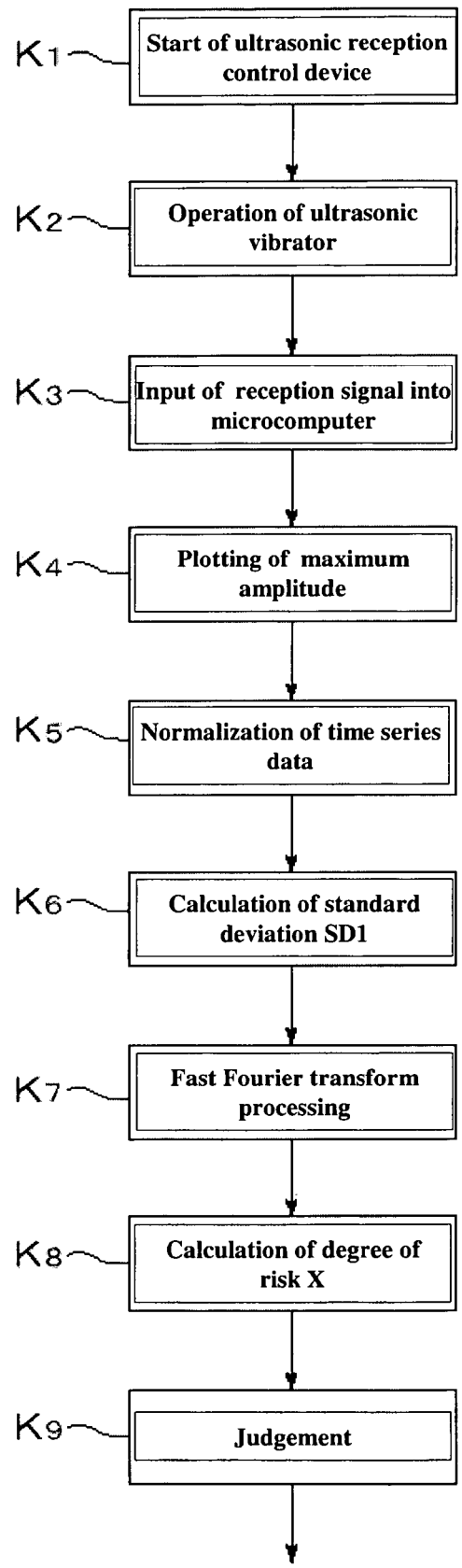

[Fig.11]
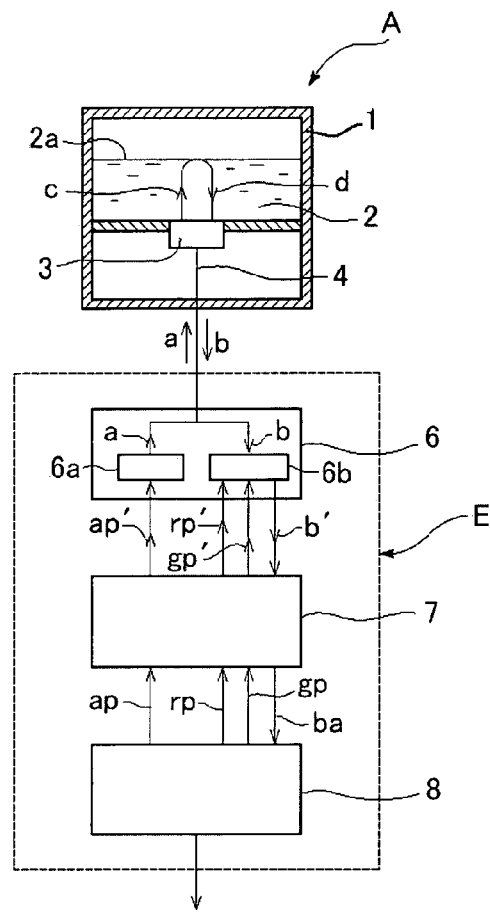
[Fig.12]
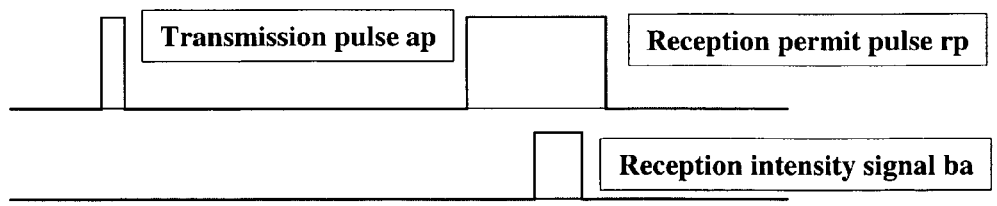

[Fig.13]
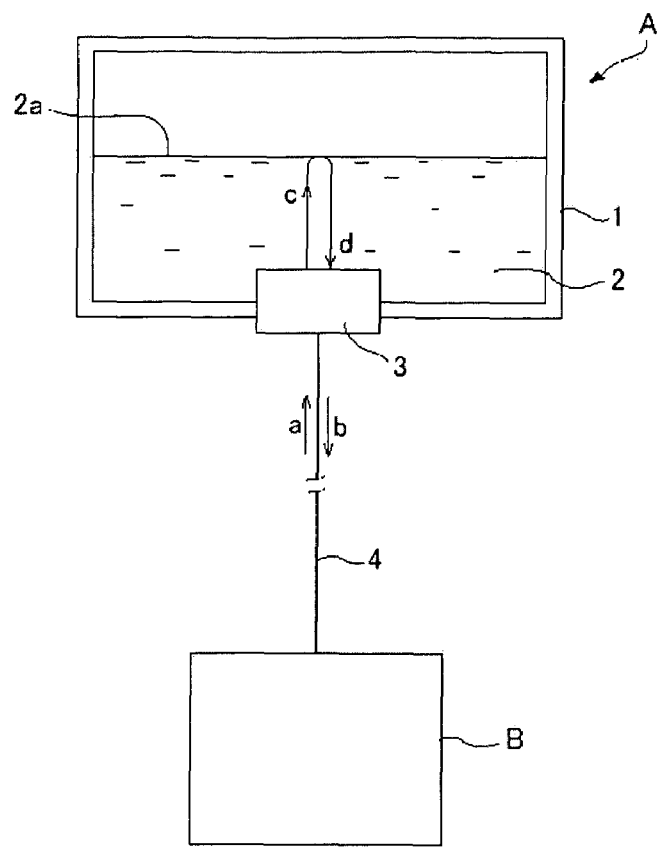
[Fig.14]
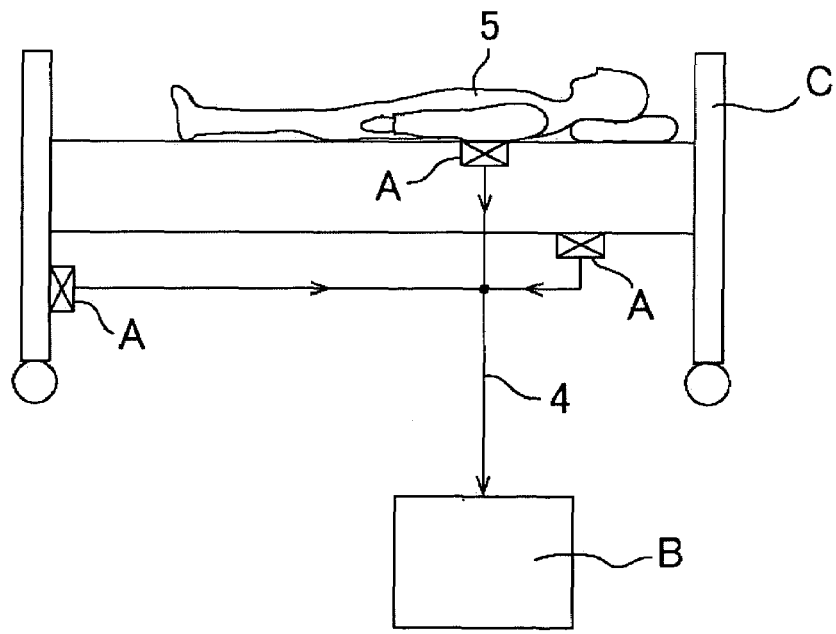

STATUS DISCRIMINATING APPARATUS OF HUMAN, ANIMAL, MACHINE OR THE LIKE USING ULTRASONIC VIBRATION DETECTING SENSOR, AND STATUS DISCRIMINATING METHOD OF HUMAN, ANIMAL, MACHINE OR THE LIKE USING THE SAME

This application claims priority to Japanese Patent Application Serial No. 2003-9041, filed on Jan. 17, 2003, the entire disclosure of which is hereby incorporated by reference.

BACKGROUND OF THE INVENTION

1. Field of the Invention

The present invention relates to a status discriminating apparatus of human, animal, machine or the like capable of discriminating normal or abnormal status of human, animal, machine or the like automatically, quickly and accurately by using an ultrasonic vibration detecting sensor, and a status discriminating method of human, animal, machine or the like by using the same, being mainly used in observation of status of inpatients in hospital, and observation of an animal, a machine or the like.

2. Description of the Prior Art

In a hospital or factory, for example, television camera systems are widely used in remote observation of inpatients and machines, and the circumstance in hospital or factory is continuously observed by monitor screens installed in a nurse station or operation room.

Further, the hospital or factory is equipped with nurse call devices, or other communication devices for transmitting the requests of patients, or the condition of machines, to the nurse's station, or operation room, by means of pushbutton operation or microphone operation, and the patients or machine operators can transmit their will freely. Examples of prior art nurse call devices, or communication devices useful for monitoring, are described in the non-patent references listed below.

Non-Patent Reference 1

1) Bio information detection by making use of pressure and acoustic changes of air mat "Studies in university"

Yoshijiro Watanabe, Assistant Professor, Hosei University Faculty of Engineering, Air mat utilization technology A Study on Sleep Stage Estimation via Non-invasive Air Mattress Sensor {SICE Annual Conference 2003 in Fukui}

Non-Patent Reference 2

2) Mat sensor confirming bed-leaving by pressure changes

"Products"

Takenaka Engineering Co., Ltd. Poriomania, bed-leaving alarm http://www.takex-eng.co.jp/shoukai/index_helth.html Technos Japan Co., Ltd. Poriomania, bed-leaving alarm http://www.technosj.co.jp/Fukushi/Haikai/Frame/haikai_top.htm In such television monitor systems, however, it is hard to discriminate a specific condition of individual patients, or machines, accurately, and it is nearly impossible to judge the breathing condition of severely ill patients in the nighttime.

The problem is the same in the nurse call system, that is, a severely ill patient cannot utilize the nurse call system.

To solve these problems, the present applicant newly developed an ultrasonic vibration detecting sensor completely different in structure and function from the existing accelerometer or vibrometer, and developed a human status measuring method using this ultrasonic vibration detecting sensor, which is disclosed in Japanese patent application Ser. No. 2002-118842.

In this human status measuring apparatus, as shown in FIG. 14, an ultrasonic measuring apparatus composed of an ultrasonic vibration detecting sensor A and an ultrasonic control device B is installed in a bed C, and human status changes (i.e., changes of vibration state) are detected by the ultrasonic vibration detecting sensor A, and analyzed by the ultrasonic control device B, so that normal or abnormal status of the human patient can be discriminated.

The ultrasonic vibration detecting sensor A is, as shown in FIG. 13, composed of a container main body 1, a liquid 2 packed in the container main body 1 so as to have a liquid level in its inside, and an ultrasonic vibrator 3 for transmitting an ultrasonic wave c into the liquid 2 and receiving an ultrasonic wave d reflected from the liquid level (i.e., the liquid surface).

The ultrasonic control device B is for controlling the ultrasonic vibration detecting sensor A so as to transmit and receive the ultrasonic waves c, d from the ultrasonic vibrator 3 into the liquid 2, and it is designed to receive and issue transmission and reception signals a, b through a cable 4, and analyze the input signal b to discriminate the normal or abnormal status of the human.

In the human status measuring method previously proposed by the present applicant, as shown in FIG. 14, the ultrasonic vibration detecting sensor A is installed properly in the bed C, and the ultrasonic control device B is provided for receiving and controlling the ultrasonic wave d reflected from the liquid level 2a by transmitting the ultrasonic wave c into the liquid 2 from the ultrasonic vibrator 3 of the ultrasonic vibration detecting sensor A, so that the human status 5 can be measured by measuring the changes of the liquid level 2a caused by the status of the human 5 by the reflected ultrasonic wave d from the liquid level 2a.

The explanation in FIG. 14 refers only to human status measurement, but this ultrasonic vibration detecting sensor can be similarly applied in measurement of status of animals, machines, etc.

The human, animal or machine status measuring method by using the ultrasonic vibration detecting sensor A in FIG. 13 and FIG. 14 previously developed by the present applicant is based on the principle of discriminating changes of status of human, animal, machine or the like from the state changes (in particular, amplitude changes) of vibration waveform of reception ultrasonic wave d detected by the ultrasonic vibration detecting sensor A, and life or death of a human or an animal, or damage of a machine can be detected and judged at a relatively high precision. In other words, the human, animal or machine monitoring method described above relies upon the detection of vibration (i.e., movement) generated by the living human or animal, or the operating machine. The absence of vibration generated by a human or animal suggests the creature is dead. Likewise, machines that are no longer operating (i.e., are "dead") do not generate vibrations.

However, the development is still halfway for quantitative determination means or measures for estimating the degree of risk leading to death of a human or an animal, or the degree of risk of leading to the breakdown of machine, from the reception of ultrasonic signal detected by the ultrasonic vibration detecting sensor A, and there are various problems to be solved until the method has practical use in patients, animals and machines. In particular, in the presence of large background noise or vibration, normal or abnormal status of a human, an animal, a machine or the like cannot be specifically judged at high precision.

In the status measuring method of human, animal, machine or the like previously developed by the present applicant, the ultrasonic control device B is composed of a conventional so-called "discrete circuit," which is an expensive circuit, and the construction expense of the system for realizing this method is soaring, and it is hard to lower the cost.

SUMMARY OF THE INVENTION

The present invention is intended to solve the problems of the status discriminating method of human, animal, machine or the like (hereinafter called "human or other status discriminating method") previously developed by the present applicant. The disadvantages of the previous system include (1) a specific means for quantitative human status discrimination at higher precision is not yet developed, so there are various problems for the actual application in monitoring human or other non-human statuses, and (2) the construction expense of the human or other status discriminating system is high, and this cost cannot be lowered significantly. Thus, it is an object of the invention to present a human or other status discriminating apparatus using an ultrasonic vibration detecting sensor capable of substantially curtailing the system construction expenses for human or other status discrimination, by discriminating the human or other status quantitatively at high precision by using the ultrasonic vibration detecting sensor A and constructing the ultrasonic control device B by using a microcomputer, and a human or other status discriminating method using the same.

The invention as set forth in a first embodiment is a status discriminating apparatus of human, animal, machine or the like using ultrasonic vibration detecting sensor comprising an ultrasonic vibration detecting sensor composed of a container main body, a liquid packed tightly in the container main body, and an ultrasonic vibrator for transmitting ultrasonic wave into the liquid and receiving ultrasonic wave reflected from the liquid surface, for detecting the behavior of a human subject to be detected, an ultrasonic transmission and reception control device composed of an ultrasonic transmitter/receiver, a signal converter, and a microcomputer, for issuing a transmission signal at every specific time interval to the ultrasonic vibration detecting sensor, receiving a reception signal at every specific time interval from the ultrasonic detecting sensor, and calculating the risk of the detection object of the ultrasonic vibration detecting sensor such as human, animal, machine or the like from the change of maximum amplitude of the input reception signal, and a cable for coupling the ultrasonic detecting sensor and ultrasonic transmission and reception control device, and forming an input and output passage of transmission signal and reception signal.

The invention as set forth in a second embodiment relates to the invention of the first embodiment, in which the microcomputer of the ultrasonic transmission and reception control device is designed as a microcomputer for compiling time series data of maximum amplitude values of reception signals entered at specific time interval from the ultrasonic vibration detecting sensor, calculating the standard deviation about the change point of a specific number of maximum amplitude values, extracting the spectrum peak by fast Fourier transform of waveform of the time series data, and calculating the human risk by fuzzy If-Then rule from the standard deviation and spectrum peak.

The invention as set forth in a third embodiment is a status discriminating method of human, animal, machine or the like by a status discriminating apparatus of human, animal, machine or the like using ultrasonic vibration detecting sensor, being a status discriminating method of human, animal, machine or the like using ultrasonic vibration detecting sensor for detecting the status of human, animal, machine or the like by detecting a vibration caused by behavior of human, animal, machine or the like by an ultrasonic vibration detecting sensor, and calculating the reception signal detected by the ultrasonic vibration detecting sensor by a microcomputer of an ultrasonic transmission and reception control device, comprising the steps of compiling time series data of maximum amplitude values of reception signals detected at specific time interval by the ultrasonic vibration detecting sensor, normalizing the time series data to form analytical data, calculating the standard deviation about the change point of maximum amplitude values in a specific number of reception signals of the analytical data, extracting the spectrum peak of ultrasonic wave by fast Fourier transform of waveform of the analytical data, calculating the human, animal, machine or other risk by applying the calculated standard deviation and extracted spectrum peak to fuzzy If-Then rule, and discriminating normal or abnormal status of human, animal, machine or the like from the calculated value of the risk.

The invention as set forth in a fourth embodiment relates to the invention of the third embodiment, in which the human, animal, machine or other risk is calculated by using a membership function expressing fuzzy If-Then rule.

The invention as set forth in the fifth embodiment relates to the invention of the third embodiment, in which the microcomputer of the ultrasonic transmission and reception control device transmits transmission pulses and reception permit pulses to the ultrasonic transmitter/receiver at every specific time interval, and controls transmission of ultrasonic wave from the ultrasonic vibration detecting sensor and acceptance of reception signal of ultrasonic wave from the ultrasonic vibration detecting sensor.

In accordance with a sixth embodiment of the present invention, a status discriminating apparatus for a human, an animal, or a machine, is claimed wherein the apparatus comprises: (a) an ultrasonic vibration detecting sensor comprising: (i) a container main body; (ii) a liquid packed tightly in the container main body; and (iii) an ultrasonic vibrator arranged to transmit an ultrasonic wave into the liquid and to receive an ultrasonic wave reflected from the liquid surface, which serves to detect behavior of a detection object; (b) an ultrasonic transmission and reception control device comprising: (i) an ultrasonic transmitter/receiver; (ii) a signal converter operably connected to the ultrasonic transmitter/receiver; and (iii) a microcomputer operably connected to the signal converter so the microcomputer issues a transmission signal, at specific time intervals, to the ultrasonic vibration detecting sensor, and the microcomputer receives a reception signal, at specific time intervals, from the ultrasonic detecting sensor, and wherein the microcomputer calculates a risk associated with the detection object from a change in maximum amplitude of the received reception signal; and (c) a cable coupling the ultrasonic detecting sensor with the ultrasonic transmission and reception control device so as to provide an input and output passage for the transmission signal and reception signal.

In accordance with a seventh apparatus embodiment of the present invention, the status discriminating apparatus according to the sixth embodiment isv further modified so the microcomputer of the ultrasonic transmission and reception control device is programmed to perform the following operations: compile time series data of maximum amplitude values of received reception signals entered at specific time intervals from the ultrasonic vibration detecting sensor, to calculate a standard deviation about a change point of a specific number of maximum amplitude values, to extract a spectrum peak by fast Fourier transform of a waveform of the time series data, and to calculate risk by a fuzzy If-Then rule from the standard deviation about the change point and the spectrum peak of the waveform. In accordance with an eighth embodiment of the present invention, the status discriminating apparatus according to the sixth embodiment is modified so that the detection object is selected for the group consisting of a human, an animal and a machine.

In accordance with a ninth embodiment of the present invention, a status discriminating method executable by a status discriminating apparatus for a human, an animal, or a machine, is claimed wherein the apparatus comprises a microcomputer operatively connected to transmit and receive signals with an ultrasonic vibration detecting sensor, the method comprising the steps of: (a) detecting vibration caused by behavior of a detection object using the ultrasonic vibration detecting sensor, which in response to vibration detection sends a reception signal to the microcomputer of the status discriminating apparatus; and (b) analyzing the reception signal sent by the ultrasonic vibration detecting sensor to the microcomputer, wherein the reception signal analysis comprises the steps of: (i) compiling time series data of maximum amplitude values of reception signals detected at specific time intervals by the ultrasonic vibration detecting sensor; (ii) normalizing the time series data to form analytical data; (iii) calculating a standard deviation about a change point of maximum amplitude values in a specific number of reception signals of the analytical data; (iv) extracting an ultrasonic wave spectrum peak by fast Fourier transform of a waveform of the analytical data; (v) calculating risk by applying the calculated standard deviation and extracted spectrum peak to a fuzzy If-Then rule; and (vi) discriminating normal or abnormal status of the detection object from the calculated value of the risk.

In accordance with a tenth embodiment of the present invention, the status discriminating method according to ninth embodiment is modified so that the risk is calculated by using a membership function expressing fuzzy If-Then rule. In accordance with an eleventh embodiment of the present invention, the ninth embodiment is modified so that the microcomputer is a component of an ultrasonic transmission and reception control device, and transmits transmission pulses and reception permit pulses to an ultrasonic transmitter/receiver of the control device at specific time intervals, and the microcomputer controls transmission of ultrasonic waves from the ultrasonic vibration detecting sensor as well as acceptance of ultrasonic wave reception signal from the ultrasonic vibration detecting sensor. In accordance with a twelfth embodiment of the present invention, the ninth embodiment is modified so that the detection object is selected for the group consisting of a human, an animal and a machine.

Further objects, features and advantages of the present invention will become apparent from the Detailed Description of the Illustrative Embodiments, which follows, when considered together with the attached drawings.

BRIEF DESCRIPTION OF THE DRAWINGS

FIG. 1 is a schematic diagram showing a basic configuration of human or other status discriminating apparatus using an ultrasonic vibration detecting sensor.

FIG. 2 shows the water level state of the ultrasonic vibration detecting sensor and corresponding waveforms of ultrasonic reception signals b', in which FIG. 2A is the status of no vibration, FIG. 2B is the status of inclination, and FIG. 2C is the status of vibration.

FIG. 3 is an explanatory diagram of application of human or other status discriminating apparatus of the invention in hospital bed;

FIG. 4 is an explanatory diagram explaining processing or analysis of data detected by the human or other status discriminating apparatus in FIG. 3, in which FIG. 4A shows plotting of maximum amplitude of data of each time obtained at intervals of 0.1 second as time series data of vibration detection, and FIG. 4B shows analytical data obtained by normalizing the plotted data.

FIG. 5 shows analytical data corresponding to FIG. 4B of the data acquired from the human or other status discriminating apparatus in FIG. 3 when the bed C is not loaded.

FIG. 6 shows analytical data corresponding to data acquired when patients are lying on the beds C, in which FIG. 6A shows patient X is lying, and FIG. 6B shows patient Y is lying.

FIG. 7 shows analytical data corresponding to data acquired by putting concrete blocks on the bed C, in which FIG. 7A shows one block of 15 kg, FIG. 7B two blocks of 15 kg each, and FIG. 7C three blocks of 15 kg each.

FIG. 8 shows results of fast Fourier transform of waveform of analytical data shown in FIG. 7, in which FIG. 8A shows the result of fast Fourier transform of waveform in FIG. 5, FIG. 8B the fast Fourier transform of waveform in FIG. 6A, and FIG. 8C the fast Fourier transform of waveform in FIG. 6B.

FIG. 9 graphically illustrates a membership function expressing fuzzy If-Then rule logic.

FIG. 10 is a systematic flow diagram explaining the steps of n method embodiment of the present invention.

FIG. 11 shows a second embodiment of a human or other status discriminating apparatus in accordance with the present invention.

FIG. 12 is an explanatory diagram illustrating the timing relation of transmission pulse "ap," reception permit pulse "rp," and reception intensity signal "ba" in ultrasonic transmission and reception control device E in the second apparatus embodiment of FIG. 11;

FIG. 13 is an explanatory diagram showing a basic configuration of ultrasonic vibration detecting sensor previously developed by the present applicant; and FIG. 14 is an explanatory diagram showing an embodiment of human or other status measuring method using the ultrasonic vibration detecting sensor previously developed by the present applicant.

DESCRIPTION OF THE ILLUSTRATIVE EMBODIMENTS

Referring now to the drawings, preferred embodiments of the invention are described specifically below, wherein like parts are referred to using like reference characters.

FIG. 1 is a block diagram showing a basic configuration of a human or other status discriminating apparatus using an ultrasonic vibration detecting sensor, and the human or other status discriminating apparatus of the invention, which is composed of an ultrasonic vibration detecting sensor A and an ultrasonic transmission and reception control device D, where A and D are connected, or coupled, by a cable 4. The same parts and members as in FIG. 13 and FIG. 14 relating to the previous development are identified with same reference numerals. Herein, the term "human or other" is defined inclusively to mean human, animal, machine or other.

The ultrasonic vibration detecting sensor A is composed of a container main body 1, an ultrasonic vibrator 3 disposed at its bottom, and a liquid 2 tightly packed (i.e., so as not to leak) in the container main body 1 so as to form a liquid level 2a in its inside. The upper side of the liquid level 2a is a blank space (i.e., air or vacuum).

The container main body 1 is made of either metal or resin, and its material is not specified. Similarly, the shape of the container main body 1 may be freely selected.

The liquid 2 may be any liquid quality as far as ultrasonic waves c, d can be propagated, and, for example, water, organic solvent or their mixed solution may be used. To adjust the ultrasonic velocity, a viscous matter may be mixed in the liquid 2, and a properly selected viscosity may be achieved.

The blank space may be filled with air or proper gas, or may be kept in vacuum state so as to fill with the saturated vapor of the liquid 2.

The ultrasonic vibrator 3 may be immersed in the liquid 2 to sink the upper surface as shown in the drawing (FIG. 1), or the lower surface may be exposed directly to the atmosphere, or the lower surface may be kept in contact with the inner bottom of the container 1.

The ultrasonic transmission and reception control device D is composed of an ultrasonic transmitter/receiver 6, a signal converter 7, and a microcomputer 8, and has various functions, for example, (1) controlling transmission and reception of ultrasonic waves, (2) converting maximum amplitude of ultrasonic reception signals d received at specific time intervals mentioned below into time series data for vibration detection, (3) calculating a standard deviation of a change point of maximum amplitude of received ultrasonic reception signals d, (4) confirming, by fast Fourier transform of received ultrasonic signals d, a feature (peak) of spectrum, (5) calculating human or other risk by using a membership function from the calculated standard deviation or confirmed spectrum peak, and (6) discriminating a normal state or an abnormal state of a human, or some other monitored status, from the calculated value of risk and the result is issued (i.e., displayed at the nurse's station, operation room, other monitoring station, or the like).

Referring to FIG. 1, the ultrasonic transmitter/receiver 6 transmits and receives ultrasonic waves c, d, respectively, through the ultrasonic vibrator 3 (center frequency 2 MHz). The received ultrasonic wave d is taken into the microcomputer 8 by way by of the signal converter 7. The center frequency of the ultrasonic vibrator is not limited to 2 MHz, but may include various other bands.

FIG. 2 shows the state of the water level 2a and waveforms of reception signal b. First, FIG. 2A shows a waveform in a state free from vibration. Since the angle formed by the water level 2a and vibrator 3 is a right angle, the transmitted ultrasonic wave c is received without practical attenuation (i.e., received wave d is approximately equal in magnitude to transmitted wave c), and the maximum amplitude of the waveform of reception signal b is the greatest, as compared with the states of other two patterns. FIG. 2B shows a waveform in a state having an angle to the water level 2a. Since the transmitted ultrasonic wave c is attenuated, the maximum amplitude of received ultrasonic wave d, and reception signal b, is lowered. Furthermore, FIG. 2C shows a state of vibration of sensor A (water level 2a). Since the water level 2a is undulated, the maximum amplitude of the waveform of ultrasonic reception signal b is varied over time.

By analyzing the time-course changes of the maximum amplitude of the waveform of ultrasonic reception signal b, this sensor A detects vibration of the detection object (human 5 or other detection object such as an animal or machine).

Table 1 shows sensitivity test results of the ultrasonic vibration detecting sensor A in FIG. 1, in which the container main body 1 is made of an acrylic material, the ultrasonic vibrator is a piezoelectric vibrator of reference frequency of 2 MHz, and the liquid 2 is water. The "container main body size" column in Table 1 shows the inside dimensions of the container main body 1. Angles 0.0 to 10.0 indicate the inclination angle of the container main body 1, and numerical values 100 to 0 indicate the attenuation rate of the maximum amplitude of the ultrasonic reception signal b of the column. Thus, in the first column wherein the inclination angle is 0.0, the numerical value 100 corresponds to the situation shown in FIG. 2a, which corresponds to minimal or no measurable attenuation (i.e., at angle 0 degree, the maximum amplitude is 100% so there is no attenuation). The remaining columns in Table 1 shows the ratio of the maximum amplitude when the inclination angle is varied from an angle of 0 degree to 10 degrees. By 9 to 10 degrees inclination, there is generally complete amplitude attenuation regardless of the size of the container.

As clear from the results in Table 1, as the inclination angle gets larger, the attenuation of amplitude of ultrasonic reception signal b increases. In other words, the magnitude of the reception signal be decreases.

TABLE 1

Sensitivity test data of ultrasonic vibrator

| Container main body size (mm) | Angle (° C.) | | | | | | | | | | | | | | |
|---|---|---|---|---|---|---|---|---|---|---|---|---|---|---|---|
| | 0.0 | 0.5 | 1.0 | 1.5 | 2.0 | 2.5 | ... | 6.0 | 6.5 | 7.0 | 7.5 | 8.0 | 8.5 | 9.0 | 9.5 | 10.0 |
| 100 × 100 × 35 | 100 | 100 | 80 | 60 | 60 | 50 | ... | 5 | 5 | 5 | 5 | 5 | 0 | 0 | 0 | 0 |
| 100 × 100 × 15 | 100 | 90 | 80 | 60 | 50 | 40 | ... | 5 | 5 | 0 | 0 | 0 | 0 | 0 | 0 | 0 |
| 60 × 60 × 35 | 100 | 80 | 80 | 50 | 50 | 30 | ... | 5 | 5 | 5 | 5 | 0 | 0 | 0 | 0 | 0 |
| 60 × 60 × 15 | 100 | 100 | 80 | 60 | 60 | 40 | ... | 5 | 0 | 0 | 0 | 0 | 0 | 0 | 0 | 0 |

TABLE 1-continued

Sensitivity test data of ultrasonic vibrator

| Container main body size (mm) | Angle (° C.) | | | | | | | | | | | | | | |
|---|---|---|---|---|---|---|---|---|---|---|---|---|---|---|---|
| | 0.0 | 0.5 | 1.0 | 1.5 | 2.0 | 2.5 | ... | 6.0 | 6.5 | 7.0 | 7.5 | 8.0 | 8.5 | 9.0 | 9.5 | 10.0 |
| 40 × 40 × 35 | 100 | 90 | 80 | 60 | 50 | 50 | ... | 5 | 5 | 5 | 5 | 5 | 0 | 0 | 0 | 0 |
| 40 × 40 × 15 | 100 | 100 | 80 | 50 | 50 | 40 | ... | 5 | 5 | 0 | 0 | 0 | 0 | 0 | 0 | 0 |
| 20 × 20 × 35 | 100 | 100 | 80 | 80 | 70 | 60 | ... | 20 | 20 | 20 | 20 | 20 | 20 | 5 | 5 | 5 |
| 20 × 20 × 15 | 100 | 100 | 100 | 80 | 80 | 60 | ... | 20 | 20 | 10 | 10 | 5 | 5 | 5 | 5 | 5 |

(Unit: %)

The human or other status discriminating apparatus of the invention is applied in an inpatient bed, and acquisition and processing of detection data by the ultrasonic vibration detecting sensor are explained.

FIG. 3 is an explanatory diagram illustrating application of the human or other status discriminating apparatus of the invention. FIG. 3 shows, in this case, detection of vibration, transmitted to the bed C by the respiration or heart beat of a patient (human) 5, by an ultrasonic vibration detecting sensor A.

First, as shown in FIG. 3, the ultrasonic vibration detecting sensor A was installed in a clinical bed (A5141 of Paramount Bed Co., Ltd.) C, and data was acquired. That is, the data to be analyzed in this system is time-course changes of maximum amplitude of reception waveforms of ultrasonic reception signals b. The reception waveforms are acquired at intervals of 0.1 second by controlling the ultrasonic transmitter/receiver 6 by using transmission pulses ap from the microcomputer 8, and maximum amplitudes of reception waveforms of ultrasonic reception signals b are detected in each case and plotted as time series data of vibration detection (also referred to as "time series vibration detection data") as shown in FIG. 4A. Then, each plotted data is normalized, and analytical data is obtained as shown in FIG. 4B.

By using the ultrasonic vibration detecting sensor A to perform this method, data was acquired in three states, that is, (1) first state, when the patient 5 is lying on the bed C as shown in FIG. 3 (patient or subject X, and patient or subject Y), (2) second state, when a concrete block is put on the bed C in FIG. 3 (15 kg×1 piece, 15 kg×2 pieces, and 15 kg×3 pieces), and (3) third state, when no load is applied (nothing is put on bed C).

The state (2) of putting a concrete block on the bed assumed, or simulated, a status of complete stop of motion of the patient 5 (i.e., patent has died or is dying), and the state (3) of putting nothing on the bed C is intended to obtain the background noise value of the baseline bed vibration.

At intervals of 0.1 second, the three states were measured 10 times each for a period of 5 minutes (total 3000 data points). It is better for improved status detection when the sampling time in measurement is shorter, and preferably the interval may be, for example, 0.01 second.

FIG. 5 shows analytical data corresponding to FIG. 4B of the data acquired from the ultrasonic vibration detecting sensor A when the bed C is unloaded (nothing is put on the bed) in the human or other status discriminating apparatus shown in FIG. 3. FIG. 5 shows very slight changes in amplitude, which is estimated to be due to the performance (i.e., vibration or electronic noise) of the signal converter 7, or the natural vibration of the foundation of the building on which the bed C is installed.

FIG. 6 shows analytical data of acquired data when a patient is lying on the bed C, which records large changes in amplitude in both living patients 5, whether the patient represented by FIG. 6a or the patient represented by FIG. 6b. In FIG. 6, peaks A and B are measurements showing large motions of the patients 5.

FIG. 7 shows analytical data of data acquired by putting a concrete block on the bed C, and when the number of blocks put on the bed C is changed, nothing is changed in the amplitude of measurements.

In the present invention, the reception signal b entered in the microcomputer 8 from the ultrasonic vibration detecting sensor A by way of the ultrasonic transmitter/receiver 6 and signal converter 7 is plotted as time series data of vibration detection of maximum amplitude at every time of detection as mentioned above, then the microcomputer 8 normalizes the data, and the analytical data as shown in FIG. 4B is obtained.

At the same time, the microcomputer 8 performs an operation on change points of maximum amplitude of detected ultrasonic reception signals b to calculate the standard deviation.

That is, standard deviation SD1 of change point (3000 points) of maximum amplitude acquired in each time of detection, and standard deviation SD2 about 10 times of standard deviation SD1 are calculated.

The former standard deviation SD1 indicates detection data variance in a short time (0.1 second interval×3000 points=5 minutes), and the latter standard deviation SD2 indicates detection data variance in a long time (5 minutes× 10 times=50 minutes). The measuring time of detection data of standard deviation SD1 and standard deviation SD2 may be properly varied to adjust status detection sensitivity.

Table 2 shows calculated values of the standard deviation SD1 and standard deviation SD2 about the ultrasonic reception signals b detected by the ultrasonic vibration detecting sensor A in each case shown in FIG. 5, FIG. 6, and FIG. 7. As evident from Table 2, there is a clear difference in standard deviations SD1 and SD2 when patients are lying on the bed C and in the other cases where there is no patient on the bed. The data from Table 2 suggests that, if the motion of the patient 5 lying on the bed C is stopped, such a relatively "vibrationless" status can be detected by the ultrasonic vibration detecting sensor A.

TABLE 2

| | | | Standard deviation | | | | | |
|---|---|---|---|---|---|---|---|---|
| | | | Patient | | | | Concrete | |
| | | | | | | | 1 block | 2 blocks | 3 blocks |
| | Data # | None | A | B | C | D | (15 kg) | (30 kg) | (45 kg) |
| SD1 | 1 | 0.00885 | 0.1186 | 0.0318 | 0.0942 | 0.0554 | 0.0103 | 0.0109 | 0.01156 |
| | 2 | 0.00909 | 0.0965 | 0.0292 | 0.113 | 0.0311 | 0.0101 | 0.0105 | 0.01144 |
| | 3 | 0.00887 | 0.0678 | 0.0735 | 0.114 | 0.0448 | 0.0102 | 0.0107 | 0.01142 |
| | 4 | 0.00891 | 0.0716 | 0.0331 | 0.132 | 0.0371 | 0.0102 | 0.0105 | 0.01162 |
| | 5 | 0.00912 | 0.0798 | 0.0302 | 0.147 | 0.0258 | 0.00982 | 0.0106 | 0.0117 |
| | 6 | 0.00947 | 0.0424 | 0.0516 | 0.121 | 0.0293 | 0.00967 | 0.0105 | 0.01176 |
| | 7 | 0.00942 | 0.0534 | 0.0442 | 0.119 | 0.0232 | 0.00951 | 0.0107 | 0.01186 |
| | 8 | 0.00947 | 0.0389 | 0.0459 | 0.102 | 0.145 | 0.00893 | 0.0104 | 0.01198 |
| | 9 | 0.00966 | 0.0535 | 0.0392 | 0.0967 | 0.0334 | 0.00953 | 0.0104 | 0.01176 |
| | 10 | 0.00988 | 0.0753 | 0.0448 | 0.0715 | 0.0240 | 0.00935 | 0.0103 | 0.01204 |
| SD2 | | 0.000337 | 0.0234 | 0.0128 | 0.0201 | 0.0347 | 0.000422 | 0.000177 | 0.000201 |

In the microcomputer 8, the waveform of analytical data shown in FIG. 7, acquired from the ultrasonic vibration detecting sensor A, is processed by fast Fourier transform (FFT) parallel to calculation of both standard deviations SD1, SD2. FIG. 8 shows results of such a fast Fourier transform, in which FIG. 8A shows the result of the fast Fourier transform of the waveform in FIG. 5 that was obtained when nothing is put on the bed C, FIG. 8B shows the result of the fast Fourier transform of the waveform in FIG. 6A that was obtained when the patient 5 is lying on the bed C, and FIG. 8C shows the result of the fast Fourier transform of the waveform in FIG. 6B. When processing the acquired data by fast Fourier transform, the time interval of acquired data may be properly varied so as to improve vibration detection.

As presented in FIGS. 8A to 8C, when a vibration sensor formed by filing a cylindrical acrylic container of inside diameter of 300 mm and height of 20 mm with water to a height of 10 mm is installed in a bed, and vibration is measured at 3000 points at a sampling time interval of 0.1 second, acquired data can be obtained for analytical processing. Under these conditions, whenhe acquired data was processed by fast Fourier transform, corresponding to data obtained by putting nothing on the bed C, no obvious spectrum peak was confirmed (see FIG. 8A). On the other hand, when people were lying on the beds, such as in the case of subjects X and Y respectively, evident spectrum peaks (FP) and (SP) were recognized near 2 MHz and near 4 MHz as shown in FIGS. 8B and 8C. That is, the spectrum peaks observed in FIGS. 8B and 8C are peaks that can not be obtained when nothing was put on the bed C, or when concrete blocks were put on the bed. These peaks are considered to be spectrum peaks due to vibration appearing only when a person 5 (i.e., such as subjects X and Y) is lying on the bed C.

The positions of spectrum peaks (near 2 MHz and near 4 MHz) are variable depending on the following factors: the shape of the vibration sensor, the type or volume of contained liquid, the sampling time interval, the duration of data acquisition time, and other conditions.

From the maximum amplitude changes of ultrasonic reception signals b, detected by the ultrasonic vibration detecting sensor A, three characteristic values were extracted (that is, standard deviation SD1 in a short time, spectrum peak FP near 2 HZ, and spectrum peak SP near 4 HZ). In particular, the standard deviation SD1 was found to be small when there was no vibration to be detected, and both spectrum peaks FP and SP were lowered when there was no vibration.

These findings can be expressed by fuzzy If-Then rule logic as shown below.

If SD1 is small or FP is small or SP is small, Then
$\mu$ abnormality (X) is high ... (1)

where $\mu$ abnormality (X) is the degree of risk associated with patient X.

This fuzzy If-Then rule is expressed by the membership function shown in FIG. 9, and the degree of risk of patient X $\mu$ abnormality (X) is determined in the following formula:

$$\mu \text{ abnormality } (X) = \max \{\mu sd1\ (X), \mu fp\ (X), \mu sp\ (X)\} \quad ((2)$$

where $\mu sd1$ is the belonging degree of SD1, $\mu fp$ is the belonging degree of FP, and $\mu sp$ is the belonging degree of SP.

When the standard deviation SD1, spectrum peak FP and spectrum peak SP are calculated using the microcomputer 8, the degree of risk of patient X $\mu$ abnormality (X) is calculated from formulas (1) and (2).

Table 3 shows the degree of risk associated with each calculated status, and the degree of risk is low when the live patient is lying on the bed C (i.e., and creating detectable vibrations), and is high when stopped still (i.e., nothing is put on bed C or a heavy inanimate object is put on bed C). That is, from the value of the degree of risk, the lying status of the patient 5 (i.e., a "normal" status corresponding to the state wherein a live patient, or other detection object, generates detectable vibrations) and the stopped still status (i.e., an "abnormal" status corresponding to the state wherein a patient, or other detection object, fails to generate detectable vibrations) can be correctly distinguished from one another.

The fuzzy If-Then rule expressed in formula (1) is disclosed in the publication by L. A. Zaden, John Witey and Sons, 1987 (hereafter, the "Fuzzy Sets Reference"), which is incorporated herein in its entirety by reference. The fuzzy If-Then rule taught by the Fuzzy Sets Reference is a known rule among those skilled in the art in the technical field of fuzzy theory.

TABLE 3

| | | Degree of risk | | | | | | |
|---|---|---|---|---|---|---|---|---|
| | | Patient | | | | Concrete | | |
| Data # | None | A | B | C | D | 1 block | 2 blocks | 3 blocks |
| 1 | 0.954 | 0 | 0 | 0 | 0 | 0.956 | 0.961 | 0.961 |
| 2 | 0.946 | 0 | 0 | 0 | 0 | 0.955 | 0.945 | 0.964 |
| 3 | 0.947 | 0 | 0 | 0 | 0 | 0.958 | 0.958 | 0.960 |
| 4 | 0.950 | 0 | 0 | 0 | 0 | 0.959 | 0.959 | 0.961 |
| 5 | 0.954 | 0 | 0 | 0 | 0 | 0.955 | 0.956 | 0.961 |
| 6 | 0.945 | 0 | 0 | 0 | 0 | 0.960 | 0.961 | 0.960 |
| 7 | 0.954 | 0 | 0 | 0 | 0 | 0.956 | 0.958 | 0.962 |
| 8 | 0.957 | 0 | 0 | 0 | 0 | 0.956 | 0.957 | 0.961 |
| 9 | 0.954 | 0 | 0 | 0 | 0 | 0.955 | 0.958 | 0.964 |
| 10 | 0.950 | 0 | 0 | 0 | 0 | 0.958 | 0.956 | 0.959 |

When the degree of risk μ abnormality (X) is calculated, the microcomputer 8 compares the calculated degree of risk with a preset value (i.e., a reference value). When the degree of risk is over the preset value, the microcomputer 8 makes the judgement or determination that the human, or other detection object, is in the abnormal status, and a warning regarding abnormal status is sent outside of the human or other status discriminating apparatus. For example, a warning signal or display could be sent to the nurse's station or to the operation room. When the calculated degree of risk is lower than the preset value, the microcomputer 8 makes the judgement or determination that the human, or other detection object, is in the normal status. Then, the normal status is indicated by transmitting a display signal, or the like, to the nurse's station, the operation room or to some other monitored area.

Execution of the method of the invention is explained next. Referring to FIG. 3 and FIG. 10, in this method embodiment of the invention, the ultrasonic vibration detecting sensor A with center frequency of 2 MHz, for example, is fixed at a proper position in the mat of the bed C of the patient 5 so as to be able to detect vibration in the bed. This ultrasonic vibration detecting sensor A is connected to the ultrasonic transmission and reception control device D by a cable 4.

Once the human or other status discriminating apparatus has been properly attached to the bed C, the microcomputer 8 is started (step $K_1$). Then, transmission pulses ap are sent to the ultrasonic transmitter/receiver 6 at predetermined intervals by way of the signal converter 7, and transmission signals a are sent into the ultrasonic vibrator 3 from the ultrasonic transmitter/receiver 6, so transmission ultrasonic waves c are transmitted. Thus begins the operation of the ultrasonic vibrator (step $K_2$). Subsequently, reception ultrasonic waves d reflected from the liquid level 2a are received by the ultrasonic vibrator 3, then reception signals b are converted into digital reception signals bp by way of the ultrasonic transmitter/receiver 6 and signal converter 7, and input into the microcomputer 8 (step $K_3$).

Within the microcomputer 8, changes points of maximum amplitude of reception signals b, entered at specific time intervals, for example, 0.1 second, are plotted as time series data of vibration detection (step $K_4$). Next, the time series data of vibration detection are normalized so that analytical data is obtained (step $K_5$).

Next, the standard deviation SD1 of a specified number of points (i.e., in a specified time) of changes points of maximum amplitude (e.g., in this embodiment, about 3000 points, in 5 minutes) is calculated in the microcomputer 8 (step $K_6$), and the calculated value of the standard deviation SD1 is stored.

The waveform of the analytical data is subsequently processed by fast Fourier transform within the microcomputer 8 (step $K_7$), and the correlation of frequency and intensity of ultrasonic wave is calculated and displayed, and spectrum peaks EP, SP are extracted.

Calculation of standard deviation SD1, and the processing of the waveform by fast Fourier transform are not necessarily specified in sequence of execution, for both operations can be simultaneously executed in parallel within the microcomputer 8.

Next, the two characteristic peak values, (FP) and (SP), obtained from the calculated value SD1 of standard deviation and fast Fourier transform of the wave form are applied in the fuzzy If-Then rule logic, and the degree of risk intrinsic to the patient 5 μ abnormality (X) is calculated (step $K_8$). Only one peak value may be applied in the fuzzy If-Then rule when there is only one peak value, or when plural peak values are present, plural peak values may be applied.

If the calculated degree of risk X exceeds the preset value, the patient is judged, by the microcomputer 8, to be in an abnormal status (step $K_9$), and this information is sent to an outside display or monitor, such as would be positioned at a nurse's station, or in an operations room, or in some other monitored area.

By operating this process consecutively or intermittently in multiple patients, the human or other status discrimination can be executed as a so-called human or other status discrimination system. For the purposes of this disclosure, steps $K_1$ and $K_2$ provide for detecting vibration using the ultrasonic vibration detection sensor A to generate reception signals, step $K_3$ provides for inputting the reception signals into the microprocessor 8, and steps $K_4$ through $K_9$ provide for reception signal analysis to determine whether the normal or the abnormal status has been detected.

FIG. 11 shows a second embodiment of the human or other status discriminating apparatus in accordance with the present invention, in which the ultrasonic transmission and reception control device E is slightly different from the ultrasonic transmission and reception control device D in FIG. 1.

In particular, in the ultrasonic transmission and reception control device E of this embodiment, transmission pulses ap are transmitted at specific time intervals, and after transmission of transmission pulses ap, a reception permit pulse rp is transmitted. By determining the timing of the two pulses ap and rp properly, reception signals b can be received without allowing saturation of the ultrasonic transmitter/receiver 6 with transmission pulses.

Reception signals b received in the ultrasonic transmitter/receiver 6 are A/D converted in the signal converter 7, and taken into the microcomputer 8. At this time, a reception gain control signal gp transmitted from the microcomputer 8 is used to adjust the reception signals b to rated values. Specifically, the intensity of reception signals b is compared with the reference preset value, and the gain is automatically adjusted by the difference so the gain of the degree of amplification of reception signal b is varied, and the output values of reception signals b are adjusted to a reference set value. The gain setting voltage is obtained by making use of a D/A output of the microcomputer 8.

By using this automatic gain adjustment, slight changes of reception signals b can be detected securely and reliably, and entered in the microcomputer 8 as reception intensity signals ba.

These reception intensity signals ba can be taken into the microcomputer 8 by A/D conversion of the reception signals b' at high speed, or the reception intensity signals ba can be also taken in by fast operation of a DSP system.

Reception signals b' can be taken into the microcomputer 8 by accumulating the intensity of reception signals, for example, by taking in the peak-hold signals by using a hold circuit of the reception signal voltage. This method is advantageous in that fast calculation can be omitted by storing the maximum intensity in signals, so that the arithmetic operation itself is simplified.

The timing of transmission pulses ap, reception permit pulse rp, and reception intensity signals ba, is basically determined as the timing shown in FIG. 12 for generating signals.

In other words, the basic cycle of the timing shown in FIG. 12 is repeated, and specified operations are executed at every specified number of times to make comparison with the basic set values so the necessary signals are generated.

In this manner, various operations (i.e., the steps), the judging method, and the threshold preset values can be freely changed, which provides more flexibility when building up such a status discriminating system.

When using the peak-hold circuit of signal intensity, after giving a reception permit and before taking in the signals, the hold signal is issued to store the maximum value, and then the stored voltage is taken in.

A transmission circuit 6a, which is a component of the ultrasonic transmitter/receiver 6 in FIG. 11, is not particularly specified as far as preparing a necessary high voltage. This high voltage is taken out as required, and given to the ultrasonic vibrator 3.

On the contrary, by preparing a low voltage, a high voltage can be generated by counterelectromotive force generated by the inductance inserted in the power supply circuit of the system, and the vibrator may be driven by utilizing this power supply circuit.

Furthermore, a reception circuit 6b, which is also a component of the ultrasonic transmitter/receiver 6, is an ordinary high frequency receiving circuit, and is composed of a so-called "amplifier circuit" and a "succeeding peak-hold circuit," and the maximum value of reception signals b is stored therein.

In the various illustrative embodiments of the present invention, the detection objects have been explained as human subjects (i.e., patients) on the bed, but the invention can be similarly applied when the detection objects are animals, or machines installed in factory, and in other suitable applications.

According to the invention, using the ultrasonic vibration detecting sensor A of small size and high sensitivity, the apparatus and method embodiments can be applied easily in beds in a hospital, or to machines in factory, and the human or other status (i.e., normal or abnormal status) can be detected securely and with high precision, which brings about excellent practical effects for the systematic discrimination of human or other statuses.

In the present invention, the ultrasonic transmission and reception control device is composed of an ultrasonic transmitter/receiver, a signal converter and a microcomputer, and specified arithmetic operations are executed by the programmable microcomputer. When compared with the case of using the ultrasonic transmission and reception control device realized by a conventional discrete circuit as developed previously, the manufacturing cost and building expense of the human or other status discriminating system can be substantially curtailed.

Furthermore, in the method embodiments of the invention, detection signals from the ultrasonic vibration detecting sensor obtained at specific time intervals are taken into the microcomputer (i.e., inputted into the microcomputer), and this microcomputer executes necessary operations, including compilation of time series data of changes of maximum amplitude in reception signals, compilation of analytical data by a normalizing process, calculation of standard deviation of changes of maximum amplitude on the basis of the analytical data, calculation and extraction of spectrum peak(s) by fast Fourier transform of analytical data waveform, calculation of degree of human or other risk by membership function expressing the fuzzy If-Then rule logic by using these arithmetic operation values, and final judgement or determination of abnormal or normal human or other status. In this manner, the human or other status can be discriminated securely, reliably, and with high precision as supported by both experiment and theory.

As described herein, the invention presents excellent practical effects of accurately judging the status of human status, animal status, machine status, and others, including life or death of a human.

While the present invention has been described with reference to certain illustrative embodiments, one of ordinary skill in the art will recognize that additions, deletions, substitutions, modifications and improvements can be made while remaining within the spirit and scope of the present invention as defined by the appended claims.

What is claimed is:

1. A status discriminating apparatus for a human, an animal, or a machine, the apparatus comprising:
  (a) an ultrasonic vibration detecting sensor comprising:
    (i) a container main body;
    (ii) a liquid packed tightly in the container main body; and
    (iii) an ultrasonic vibrator arranged to transmit an ultrasonic wave into the liquid and to receive an ultrasonic wave reflected from a surface of the liquid, which serves to detect behavior of a detection object;
  (b) an ultrasonic transmission and reception control device comprising:
    (i) an ultrasonic transmitter/receiver;
    (ii) a signal converter operably connected to the ultrasonic transmitter/receiver; and
    (iii) a microcomputer operably connected to the signal converter so the microcomputer issues a transmission signal, at specific time intervals, to the ultrasonic vibration detecting sensor, and the microcomputer receives a reception signal, at specific time intervals, from the ultrasonic detecting sensor, and wherein the microcomputer calculates a risk associated with the detection object from a change in maximum amplitude of the received reception signal; and
  (c) a cable coupling the ultrasonic detecting sensor with the ultrasonic transmission and reception control device so as to provide an input and output passage for the transmission signal and reception signal.

2. The status discriminating apparatus according to claim 1, wherein the microcomputer of the ultrasonic transmission and reception control device is programmed to perform the following operations: compile time series data of maximum amplitude values of received reception signals entered at specific time intervals from the ultrasonic vibration detecting sensor, to calculate a standard deviation about a change point of a specific number of maximum amplitude values, to extract a spectrum peak by fast Fourier transform of a waveform of the time series data, and to calculate risk by a fuzzy If-Then rule from the standard deviation about the change point and the spectrum peak of the waveform.

3. The status discriminating apparatus according to claim 1, wherein the detection object is selected for the group consisting of a human, an animal and a machine.

4. A status discriminating method executable by a status discriminating apparatus for a human, an animal, or a machine, wherein the apparatus comprises a microcomputer operatively connected to transmit and receive signals with an ultrasonic vibration detecting sensor, the method comprising the steps of:
  (a) detecting vibration caused by behavior of a detection object using the ultrasonic vibration detecting sensor, which in response to vibration detection sends a reception signal to the microcomputer of the status discriminating apparatus; and
  (b) analyzing the reception signal sent by the ultrasonic vibration detecting sensor to the microcomputer, wherein reception signal analysis comprises the steps of:
    (i) compiling time series data of maximum amplitude values of reception signals detected at specific time intervals by the ultrasonic vibration detecting sensor;
    (ii) normalizing the time series data to form analytical data;
    (iii) calculating a standard deviation about a change point of maximum amplitude values in a specific number of reception signals of the analytical data;
    (iv) extracting an ultrasonic wave spectrum peak by fast Fourier transform of a waveform of the analytical data;
    (v) calculating a risk value by applying the calculated standard deviation and extracted spectrum peak to a fuzzy If-Then rule; and
    (vi) discriminating normal or abnormal status of the detection object from the calculated risk value.

5. The status discriminating method according to claim 4, wherein the risk value is calculated by using a membership function expressing fuzzy If-Then rule.

6. The status discriminating method according to claim 4, wherein the microcomputer is a component of an ultrasonic transmission and reception control device, and transmits transmission pulses and reception permit pulses to an ultrasonic transmitter/receiver of the control device at specific time intervals, and the microcomputer controls transmission of ultrasonic waves from the ultrasonic vibration detecting sensor as well as acceptance of ultrasonic wave reception signal from the ultrasonic vibration detecting sensor.

7. The status discriminating method according to claim 4, wherein the detection object is selected for the group consisting of a human, an animal and a machine.

* * * * *